United States Patent [19]
Moulton, III

[11] Patent Number: 5,575,078
[45] Date of Patent: Nov. 19, 1996

[54] ZERO LOAD THICKNESS CALIPER

[75] Inventor: James E. Moulton, III, Porter Corners, N.Y.

[73] Assignee: Hollingsworth & Vose Company, East Walpole, Mass.

[21] Appl. No.: 396,972

[22] Filed: Mar. 1, 1995

[51] Int. Cl.$^6$ .............................. G01B 7/06; G01B 5/06
[52] U.S. Cl. ...................... 33/815; 33/501.02; 33/501.03
[58] Field of Search ...................... 33/815, 821, 501.02, 33/501.03

[56] References Cited

U.S. PATENT DOCUMENTS

| | | | |
|---|---|---|---|
| 2,741,848 | 4/1956 | Livingston | 33/815 |
| 2,878,571 | 3/1959 | Johnson | 33/815 |
| 3,166,851 | 1/1965 | Shirakura et al. | 33/815 |
| 3,757,423 | 9/1973 | Wieg . | |
| 4,118,871 | 10/1978 | Kirkham . | |
| 4,335,517 | 6/1982 | James et al. . | |
| 4,813,151 | 3/1989 | Hajdukiewicz et al. | 33/832 |
| 4,866,643 | 9/1989 | Dutler | 364/571.02 |
| 5,433,015 | 7/1995 | Mazenet | 33/815 |

FOREIGN PATENT DOCUMENTS

| | | | |
|---|---|---|---|
| 81401 | 7/1981 | Japan | 33/815 |
| 26801 | 2/1986 | Japan | 33/815 |
| 2153533 | 8/1985 | United Kingdom | 33/501.02 |

OTHER PUBLICATIONS

Thwing–Albert Instrument Company, Operating Instructions for the Model I Electronic Thickness Tester (Jun. 1991).

Thwing–Albert Instrument Company, Price List #89–1–D (Jan. 1989).

*Primary Examiner*—Christopher W. Fulton
*Attorney, Agent, or Firm*—William C. Geary, III; Nutter, McClennen & Fish, LLP

[57] ABSTRACT

A caliper or measurement apparatus for compressible sheet material includes first and second opposed contact faces which move relative to each other. A load cell in one face detects the load exerted there against, while a position indicator indicates the distance between faces. A microprocessor monitors load and position values continuously, corrects the load signal for noise and drift and determines whether a change in load cell output is correlated with advance of the measurement face. When a coupled load/position pattern is identified as a compression curve, the second contact face is assumed to have contacted the sheet and a thickness value is derived from the signals. Preferably, signal values are scaled and the processor operates on integral values, resulting in fast arithmetical operations that proceed in real time as the sensors are polled at a rate in excess of several kilohertz. Once contact is achieved, the processor stores load and position values which form a compression curve, and may implement further processing to produce other empirical measurements. A bulk ZLC measurement is equal to the zero-load intercept of a tangent to a linear region of the compression curve, while fixed-load relaxed measurements, such as TAPPI measurements, are advantageously taken by applying a fixed static load in the linear compression region of the specimen. All three measurements may be taken in succession as the caliper closes.

19 Claims, 6 Drawing Sheets

ZERO LOAD THICKNESS CALIPER

BACKGROUND OF THE INVENTION

The present invention relates to measuring devices, and in particular to thickness measuring devices for measuring the thickness of sheet material such as plastic, paper, fabric, non-woven textile and the like. Many sheet materials, such as metal foil, rolled sheet metals, and hard or highly crosslinked polymer sheet, are readily measured with a high degree of repeatability using simple hand instruments such as screw-threaded micrometers or dial micrometers, or by using automated machine measurement instruments. By contrast, compliant or soft sheet materials often are made of fibrous matter so that they have a poorly defined edge extent and possess a fuzzy band of matter extending outside of the nominal plane of the sheet, making mechanical and even optical measurement equipment inappropriate; also when a major portion of their body is soft and compressible this may make measurement repeatability problematic. By way of example, rag papers and particularly thicker rag papers such as lithographic and etching papers may possess both surface roughness and a compressibility which, moreover, may vary considerably depending on environmental factors such as relative dryness due to the ambient air.

Traditionally, such materials are best measured by placing a stack of sheets, 5, 10, or 50 layers thick, between the sensing jaws of a measurement apparatus, and applying a specified compressive load for a certain period of time, before taking a measurement. This eliminates the high degree of variation caused by the relatively compressive fibrous face on the external surface of a single sheet, and averages the bulk compressibility over a large number of sheets to get a more representative measurement. A number of related protocols have been developed for obtaining standardized and ostensibly more accurate measurements for such compressible materials.

It will be appreciated, however, that a measurement which involves an average over many sheets of material taken in a compressed form under static conditions, while tending to produce a definite number, is a highly artificial measurement. Thus, it is possible for two sheets of substantially different compressibility and different fibrous make-up, to have the same nominal thickness when measured by a compression/stabilization protocol of this type. In practice, thickness measurements on compressible or non-woven webs of materials may be useful to understand the behavior—e.g., image-receptive properties, wetability etc.—of the outer surface, which is precisely the portion that is compressed and not measured in a standard protocol. Thickness measurements may also be necessary for the adjustment and proper operation of complex machinery which employs web material, such as printing, binding, calendaring, or surface treatment machinery in which adjustment of the spacing between opposed rollers, adjustment of the load exerted by a roller, or more complex adjustments involving tensioning mechanisms, inking mechanisms or processing machinery adjustments, are to be optimized based on the thickness of only a single sheet of material passing through in its generally uncompressed, or instantaneously compressed state. Thickness measurements may also be desirable in a paper-manufacturing process line, in which detected characteristics may be used to adjust processing machinery or to alter the feedstock. Thus, it would be highly desirable to develop a measuring instrument capable of performing a thickness measurement on a single sheet or web of compressible or springy material, which dependably and repeatably measures the actual thickness of the material rather than a net or average thickness of the material after a preconditioning step or interaction with the measurement device.

SUMMARY OF THE INVENTION

Accordingly, it is an object of the invention to provide a measurement instrument for sheets of compressible material.

It is another object of the invention to provide a measurement instrument for sheets of material having a fibrous texture, a compressible body, or both.

It is another object of the invention to provide such a measurement instrument which produces a dependable and repeatable measurement of sheet thickness independently of the compressive characteristics of the sheet.

It is another object of the invention to produce a measurement instrument for measuring the thickness of sheets of material, which produces sensitive and repeatable measurements, yet adapts readily to strenuous and noisy environments which might impair sensitivity.

It is another object of the invention to provide a measurement apparatus for sheet material in which measurements are performed automatically.

It is another object of the invention to provide a measurement apparatus for sheet material which produces sensitive and repeatable measurements of sheet thickness without compressing the sheets.

It is another object of the invention to provide a sensitive and repeatable measurement of sheet thickness which is equal to a conventional bulk thickness measurement yet does not require time-consuming or condition-altering preconditioning of the sheet.

These and other objects are attained in a measurement apparatus according to the present invention wherein a first contact face supports one side of a sheet article to be measured, a movable contact face, also referred to as a measurement foot below, moves against the opposite side of the article and a load cell connected to one contact face monitors the load on the sheet as the two contact faces approach each other. As the position of the movable contact face changes, a microprocessor continuously receives and monitors the load and position signals, and the monitored signals are compared against quiescent state signals and a noise band parameter to immediately identify when contact is made. The monitored load/position coordinates are temporarily stored, so that when the processor confirms actual contact, an accurate indication of the position coordinate at initial contact, or zero-load thickness measurement, is available by referring back to the position at which the first indication of coupling of the load-position parameters was first detected.

In a preferred embodiment, the load and position signals are sampled at a high frequency, e.g., over one thousand times per second and as much as one hundred thousand times per second, and the signals are digitized, providing a typical jumpy or noisy electronic signal. A processor executes a control algorithm which determines the current average signal level and sets a noise band for the load signal as the movable contact approaches the measurement site. The expected signal level and noise band are each adaptively increased as ambient conditions such as vibration or temperature produce greater signals or signal variation in the quiescent load cell signal. When the processor detects a load signal outside the current noise band, the current load and position coordinates are stored and the next several load/position pairs are inspected to determine whether there exists a pattern of monotonic coupling which would indicate that the contact force is applying an increasing load to the sheet as it advances. If the pattern confirms such coupling as the measurement foot advances several ten-thousandths of an inch, then the stored first contact position is identified as the zero load thickness measurement. In one embodiment, load/position pairs after the first contact are accumulated to form a compression curve from which the processor derives a conventional measurement specified by the Technical Association of the Pulp and Paperboard Industry (TAPPI measurement), or other bulk measurement by graphic analysis for comparison or reference purposes. The zero load or initial contact position measurement allows process machinery to be set up in the field based on the actual current thickness of a single sheet of material being fed or output at that moment in time. Suitably adapted, the apparatus may mount in a process line and periodically sample the thickness of a web passing between its jaws. Thus, it may be used for monitoring web thickness at the output of a web-making plant, or for measuring thickness in order to set process adjustments at an intermediate stage of web manufacture or processing.

BRIEF DESCRIPTION OF THE DRAWINGS

These and other features of the invention will be understood from the specification herein, taken together with the claims and the drawings appended hereto, wherein

DETAILED DESCRIPTION

Figure 1:
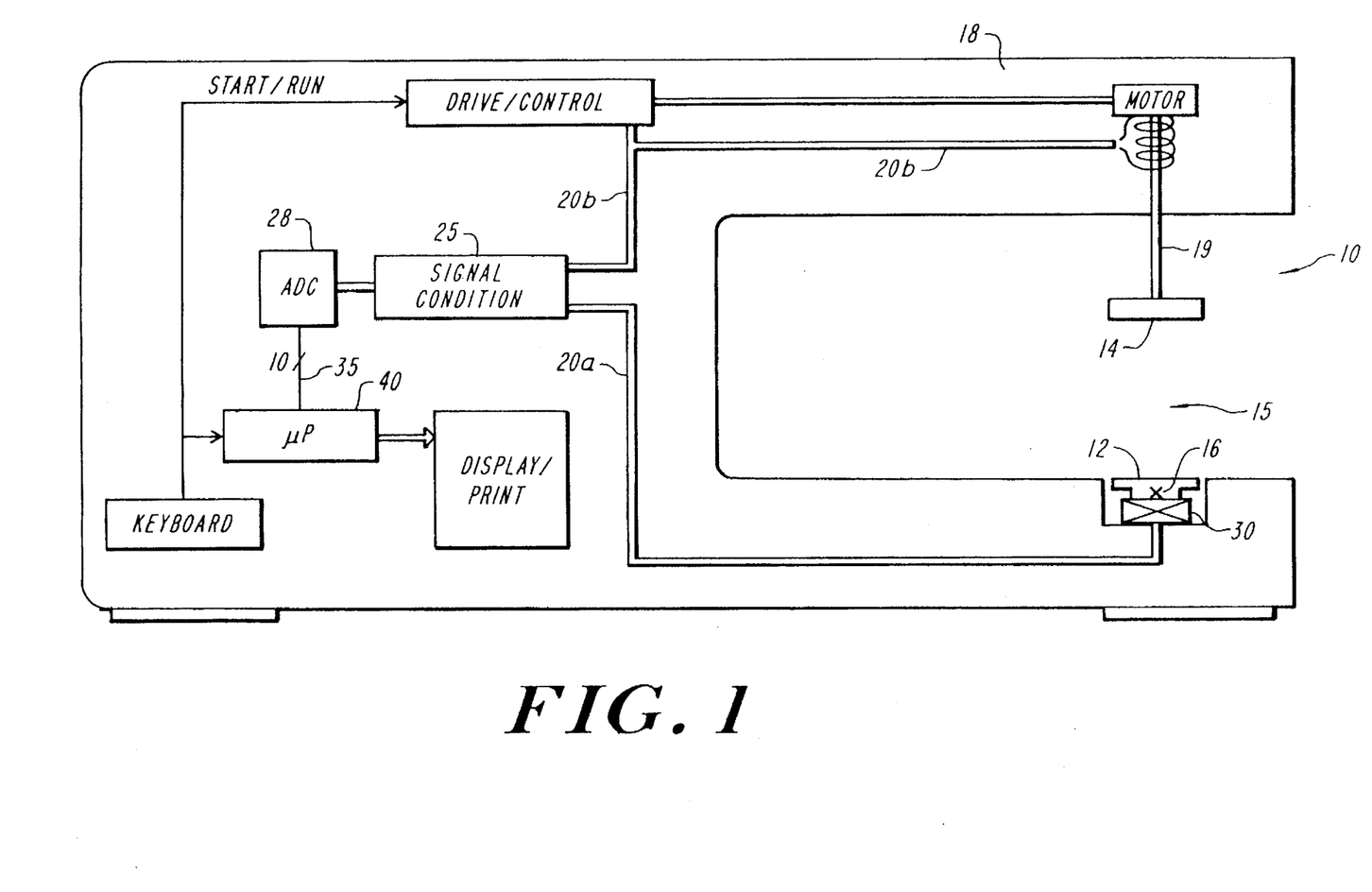
FIG. 1 illustrates a thickness measurement apparatus in accordance with the present invention.

FIG. 1 shows in broad, partly schematic representation a thickness measurement apparatus 10 in accordance with the present invention. Apparatus 10 includes a first contact face 12 and a second contact face 14 which are opposed to each other across a gap 15 defining a thickness measurement gap. Contact face 12 is situated on an anvil 16 which provides a preferably flat resting table upon which a sheet or other workpiece rests. Contact face 14, on the other hand, is connected to an arm 18, and is located at the end of a movable plunger 19 extending from the arm. The anvil 16 contains a load cell 30 which responds to the weight or force exerted on the anvil by an object placed thereon, whereas the plunger assembly 19 supporting the second contact face is connected to a position indicating system which produces an output representative of the current position of the plunger. A controller, discussed further below, monitors both outputs to detect force as a function of position and implements several analyses in order to derive an accurate and reproducible measurement of the thickness of an article placed on the anvil.

By way of example, the load cell 30 may be a model 208B dynamic force sensor made by PCB Piezotronics, Inc. of Depew, N.Y. This load cell has a range of zero to ten pounds with an output signal level between ±2.5 volts. The position measurement apparatus is capable of resolving measurements of one ten-thousandths of an inch, and has a full scale range of approximately 0.08 inches with mechanical limit stops to prevent damage to the assembly. The entire upper body together with the arm plunger and contact face with position sensing apparatus may be taken from a suitably modified model 89-1 automatic thickness gauge, sold by the Thwing-Albert Instrument Company of Philadelphia, Pa. That unit consists of a case, a frame, an electric motor and mechanical and electrical components to lower and raise a measuring foot. Position determinations are made with a linear variable differential transformer-type sensor and support electronics. The support electronics drive circuitry produces a sensitivity of approximately 51 millivolts per thousandth of an inch, with electronic controls to limit the range of movement to 0.04 inches. With these characteristics and a driving/polling rate of approximately 2500 samples per second or more, the cycle time for raising and lowering the foot to take a measurement is approximately five seconds. As noted above, for implementation of the present invention, the Thwing-Albert unit is modified to accommodate a load cell in the anvil and, as described more fully below, to accommodate a further computer board which implements processing and control functions correlating load and position data as described later herein.

As further shown in FIG. 1, the position indicator and the load cell each communicate by separate sets of leads 20b, 20a with a signal conditioning circuit 25 which, in turn, provides a conditioned signal to an analog to digital converter ADC 28, producing ten bit output words which pass on line 35 to the processor 40. The signal conditioning circuit 25 shifts the position measurement signals (nominally −1 to +4 volts) to a zero to five volt signal with a gain of 1.049. The output of the load cell and associated circuitry, which is nominally between −2.5 and 2.5 volts with a working range between ±1 volt, is shifted by the conditioning circuit to an output signal between zero and five volts with a gain of 2.048. Thus, both the load and position signals are normalized to a 0–5 V range. By shifting and scaling each signal level in this fashion to between zero and five volts for processing by the ADC 28, the conversion produces an integral representation of each signal, and the processing described further below may be effected using simple addition, comparison and multiplication operations that proceed in real time as the sensors are polled at a rate in excess of several kilohertz. Resolutions of approximately one ten-thousandth of an inch in position and two one-thousandths of a pound in force are achieved with simple arithmetical processing in short measurement cycles.

Continuing with the description of FIG. 1, the digitized signals from ADC 28 are fed to a processor 40 which, in the prototype embodiment, is a model RTC180 single board computer using a Hitachi HD64180 processor running at 9.216 megahertz. This board is sold by Micromint, Inc., of Vernon, Conn. and is a typical data acquisition and instrument control board, running programs in a modified BASIC, Micromint BASIC-180, with an on-board 32 kilobyte EPROM and 64 kilobytes of static RAM for acquired data and system variables. The control processor checks the positions of switches, operates the moving motor to advance the contact face and plunger arm, acquires the raw contact position and anvil load data signals from ADC 28, and analyzes the data as described further below, representing it with a display of status and measurement results.

By way of brief overview of measurement system operation, the microprocessor is loaded with a control program which samples the load and position data at a high rate of speed, e.g., 2500 times per second in the prototype embodiment as the plunger arm is advanced toward the anvil. It then analyzes the acquired data pairs. The load cell is a piezo element which responds quickly to changes in pressure or strain by modifying its charge level within approximately ten microseconds to produce a change in output proportional to the pressure or load change. However, due to the nature of the electronic conditioning circuits and relaxation phenomena in the piezo element, the charge then drops to approximately one third of its original value over the course of the next fifty seconds or so. That is, the load cell produces a slowly-changing output, that at any given instant, responds quickly to changes in force. The signal processor is set up to continuously adapt its processing to account for longer-term drift and to update the current average signal level and noise band while it waits for a definitive pattern of load/position data to indicate that contact is achieved and that the measurement foot has touched the outer thickness of the article being measured on the anvil. By way of example, below, an article such as a sheet of paper will be assumed.

It will be understood that the piezo element responds strongly to noise and vibration, and the load cell output is a typical noisy electrical signal such that the plurality of discrete measurements taken at intervals of several ten-thousandths of a second consist of a scattered set of voltage values which, at any given time, lie within a noise band about a mean value. The microprocessor continuously monitors and smoothes this set of signal points in the acquired data to determine a current mean value and noise band. Detection of contact is then made when a load outside the noise band occurs and meets certain criteria.

Figure 2:
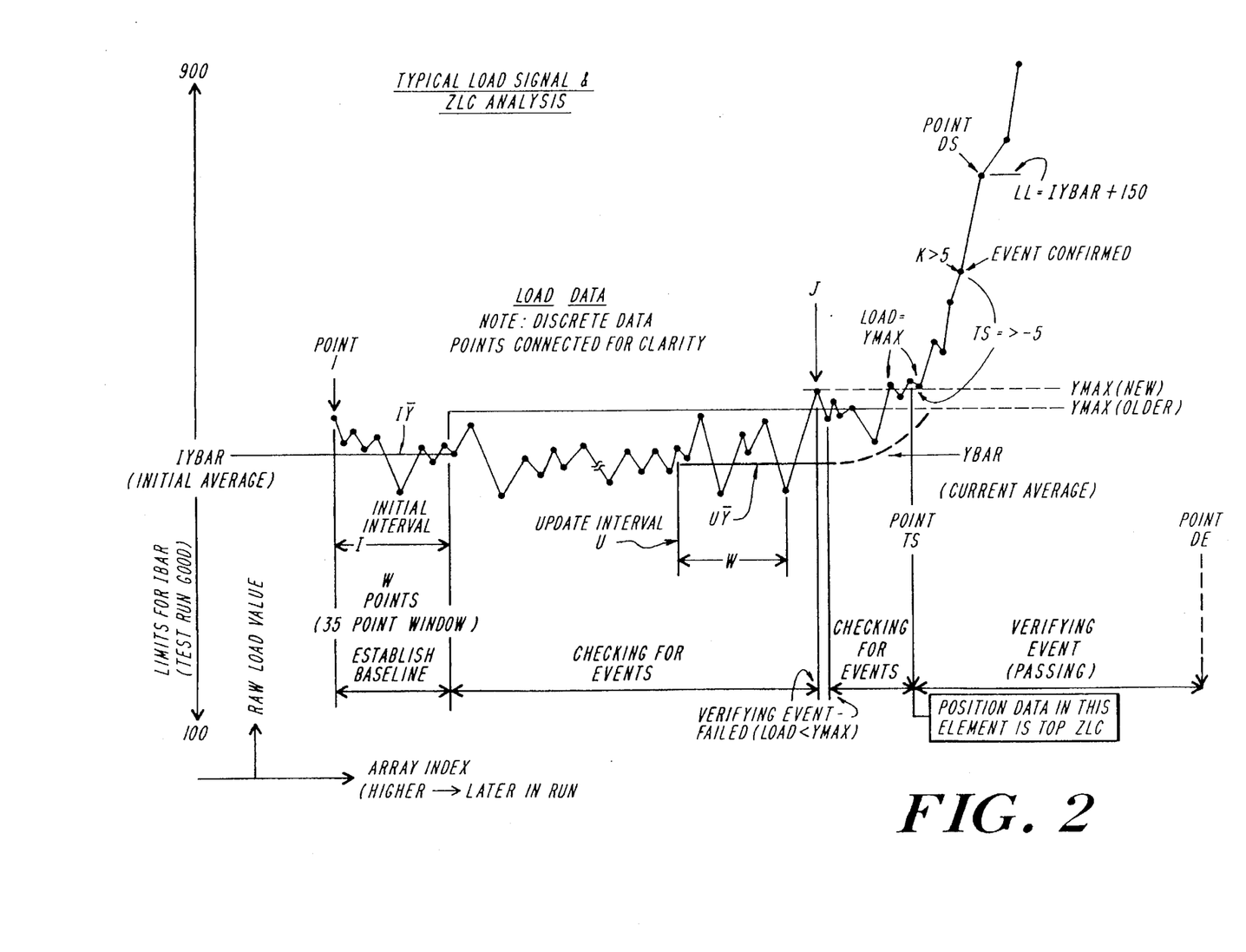
FIG. 2 illustrates intermediate measurement values of the measurement apparatus of this invention.

FIG. 2 illustrates in graphic terms the signal processing involved. Load cell output is plotted along the Y axis, while increasing co-ordinates along the X axis correspond to sampling points later in time. FIG. 2 shows an initial period I in which load signals are detected and an initial average load value $I\overline{Y}$ is derived for an initial set or window of w measurement points. A 35 point window was used to establish the baseline. The extreme values detected during this window establish a noise band, shown as a symmetric band extending ±n above and below the average value. Thereafter, during a lengthy course of monitoring as the caliper is incrementally advanced, i.e., is stepped closed on the measurement sample, the processor continues to detect load cell output values which are checked for events which trigger special discrimination protocols described further below. As the processor steps through successive load values, the average output value $I\overline{Y}$ and the noise band "n" are updated in a further window commencing with such detection, as shown by the updated region U and new or updated average $U\overline{Y}$. When a load value falls outside the noise band, as shown at point J, a verification procedure is undertaken to determine whether this simply represents a general change in signal conditions, so an updated signal level or new noise band is appropriate, or whether the load values are changing in a fashion substantially coupled to the changing measurement foot position, thus indicating that the caliper is contacting the sheet. In the latter case, illustrated at the extreme right portion of FIG. 2, the processor confirms that the calipers have contacted the sample, and among the most recent signals identifies the position at which contact is deemed to have occurred.

Thus, the overall approach is to establish a baseline load and noise band, monitor and update these parameters, and then attempt to confirm whether contact has occurred at any time an out-of-band condition is sensed. Upon verification of contact, a determination is made of the first position corresponding to the moment of contact of the movable face to the sheet being measured, and this position is taken as a zero-load thickness measurement. After the zero load contact point, as the load increases, the controller may stop the contact face from closing after a certain threshold or limit load is achieved, thus developing a steady state compressed load thickness measurement, or the controller may accumulate load/position pairs to determine the shape of the compression curve. It may then count back to an intercept of the compression curve, or may implement simple protocol to extrapolate or derive any of several conventional compressed state measurements. Preferably, the caliper is controlled by the microprocessor to take a number of measurements in quick succession and display as an output the average of the caliper and its variation. The programming is flexible, and the instrument may accumulate load/position data, and subsequently perform processing to display the measured thickness, or all processing may be performed in real time with continuous display of the closing contact position and detected thickness value.

With reference to the flow chart, FIG. 3, detailed operation of the microprocessor control portion of the instrument proceeds as follows. As noted above, the prototype embodiment was implemented by modification of a conventional automated thickness gauge in which the upper caliper face is a measurement shoe that is automatically advanced into contact with a workpiece, and a microprocessor detects and records the position information. The caliper is equipped with a top dead center switch indicating when the upper jaw is fully retracted, and basic initialization programs which retract the jaw at the start of each measurement cycle. The top dead center position signal is used in the present invention to coordinate additional load cell/position indicator processing described below.

The processing will be described with reference to a stream of load/position pairs which are successive, in the sense that they are acquired as the measurement face, coupled to a linear variable transformer, is advanced without stopping or reversing, so the pairs are arranged in a sequence corresponding to the successive positions of the measurement foot. The set of data pairs may be a stream in real time acquired as the foot moves, or may be a stored sequence of data pairs which have been taken and stored in memory as the instrument makes several successive measurement runs in a row. In that case, the data are then analyzed later as described below. For simplicity of narration below, the description is phrased in terms of a real-time stream, with descriptive phrases like "the next data point" or "as the foot advances". This is done simply to avoid the awkwardness of continually referring to the correspondence between position of the foot during the procedure and the position coordinate generated when the foot is at such position. It will be understood, however, that the only effective difference between performance of the analysis on a stored data stream, or a realtime sequence of position/load data pairs, is that in the latter case the processing must occur as fast as the measurement foot is advancing, and be performed on several thousand measurements per second. Several simplifications of signal range and type of processing are described which allow the necessary analysis to be performed at this rate with a relatively simple control processor.

Figure 3:
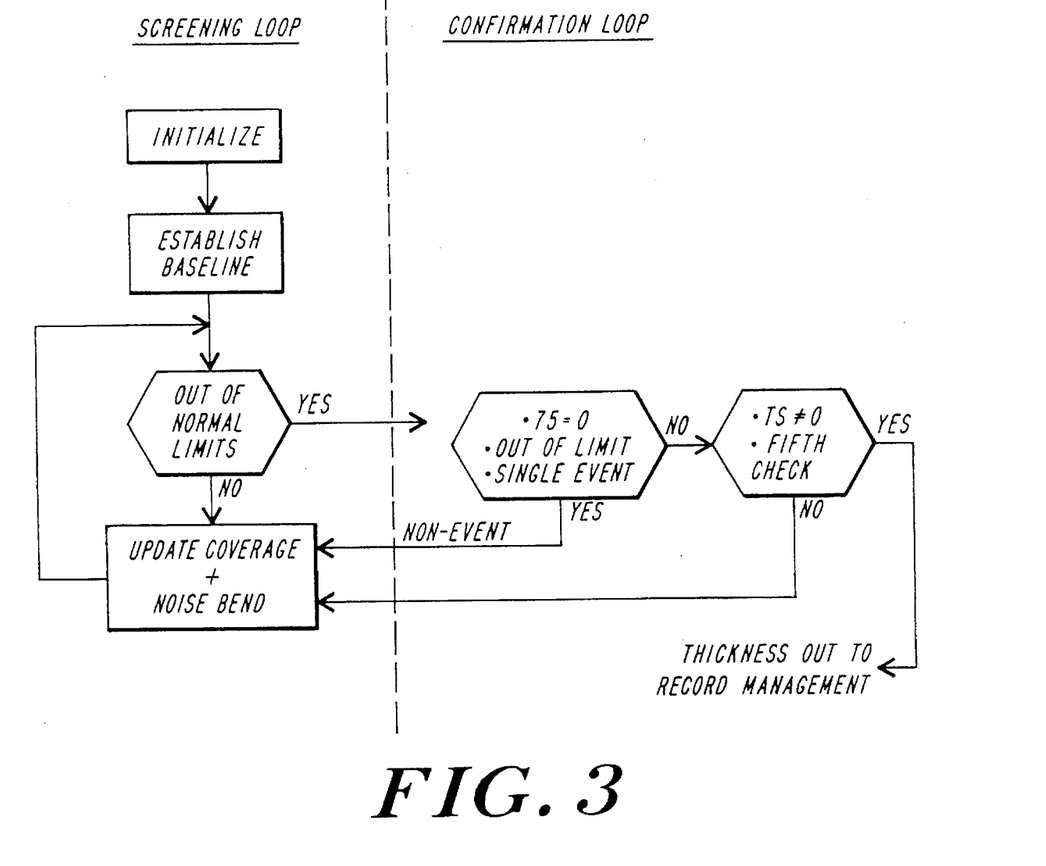
FIG. 3 shows a partial flow chart for operation of the apparatus and processing therein.

As shown in FIG. 3, during an initial period following top dead center, as the measurement foot advances but has not yet contacted the workpiece, the processor establishes a baseline measurement of the normalized load cell output value under a no-load condition. The initial sampling window consists of 35 sample points and the processing simply takes the arithmetic mean of these values and derives a measure of expected signal variation. Thus, it may perform linear regression analysis, or simply a sequence of comparisons to detect the maximum spread from the mean value, which is the noise band expected if the signal does not change characteristics. This corresponds, for example, to the $\overline{Y}+3\sigma$ statistical measurement commonly employed for setting a noise band in process control applications. When using a microprocessor of limited capability, the average $\overline{Y}$ is most easily implemented with $2^m$ data points, so that it is only necessary to add the points and drop the m least significant bits rather than employ division which is computationally more complex. Similarly, the noise band may be set to be simply a constant, or the difference between highest and lowest values in the current window, or a fractional or integral multiple of this difference, rather than employing one of the generally more complex statistical measures of variation involving square root operations. Such implementations allow the above-described microprocessor to process the data stream in real time at an acceptable measurement rate.

Once the average load is determined, this computed average is then compared to a fixed limit which has been selected in relation to the normal output values of the load cell, and if it is beyond that limit, as could happen if there were a faulty electrical circuit, or a jammed mechanical component placing an extreme load on the cell, then the processor delivers an error message and aborts the procedure. Otherwise it proceeds to initialize a number of internal variables used for run-to-run information gathering and other variables used within a single measurement run. In the prototype embodiment the variables used within each measurement cycle include, for example, an array position marker, the mean value and noise band (in this case the initial values calculated for the initial window), and the analysis window size. The window consists of the most recent set of analysis points. The initial window size is 35 data pairs, with subsequent analysis windows consisting of the current data pair and enough recent pairs to perform the determination involved. The determination of an average signal and noise band may be made with a fixed size window consisting of the most recent thirty-five data points, whereas the determination of occurrence of contact during a confirmation loop described further below, may require generally a smaller number, about five to seven, such data points. Furthermore, the window size may adaptively vary with the quality of the load signal, with larger numbers of sample points being taken when great variability is found in the load signal and smaller numbers during quiet periods. According to a preferred embodiment of the invention for real time applications, the analysis window is taken over a number of points which is a power of two and the incoming data pairs are placed in a stack, so that the most recent $2^n$ data points are available at the input buffer at each instance in time. As noted above, the load and position signals have been normalized to a 0–5V range to allow entirely integer representation. By employing a window of $2^n$ points with shift registers to store the current array of load coordinates one can entirely avoid use of division in computing signal mean values and noise band, performing the processing below with a small instruction set and a microprocessor of limited speed and memory as described.

Returning now to the description of FIG. 3, once the baseline load signal has been established and the system initialized during advance of the measurement foot, the microprocessor continues in a screening loop wherein each load value is compared to the maximum expected non-event load, that is, the current average plus noise band value. If it is greater than that value, the processor enters a confirmation loop which performs more detailed analysis of load/position data around that point to determine what is going on. The screening loop also compares the current load value to a value which is equal to the initial mean load plus the maximum expected event load. For example, with the above-described system the measurement foot is set up to accommodate a thin sheet on the anvil, and the sheet plus contact force should never occur with a force greater than one pound, so the screening may set a load value for the maximum expected load event of one pound. If a current load value greater than this is encountered, indicative of a potential error, then control again is passed to the confirmation loop, which actuates appropriate warning or alarm displays. Otherwise, that is if neither a potential "event" nor an excessive load is detected, the screening loop proceeds to update the average load value and the expected variability or noise band, and the window is shifted ahead by one to include the next data point. The screening loop then continues to screen current load values, and calls the confirmation loop for the two conditions described above.

It should be noted at this point that the load sensor is a piezo element, and as such is liable to produce an extreme signal spike in response to shock waves or the like. Since these signals may be highly uncorrelated in amplitude with actual load conditions, they are excluded from the averaging operation of the screening loop. In general the incoming data pairs may be taken at a fast rate determined by the ADC 28, typically 2500 measurements per second, corresponding to motion of the measurement face by a small fraction of its total travel, e.g., five to fifty thousandths of an inch per second. Thus, the exclusion of a small number of extreme load signal values will have no adverse effect on the overall speed, range or continuity of measurements.

The purpose of the confirmation loop is to detect what caused control to be passed to it, and identify when contact with the workpiece has been established. When the screening loop has detected a potential event, before passing control to the confirmation loop the screening loop sets a pointer TS, the top surface pointer, to point to the current position coordinate under analysis. TS is initially set to point to zero, so the zero marker indicates both the initial data position and acts as a flag meaning no position has yet been set. Thus when the confirmation loop acts on data sets, one variable TS equals current position is available as a tentative identification of the initial contact for thickness measurement. The confirmation loop performs the following test. Upon entry, it counts the number of times the loop has been consecutively executed including the current one, and it gets the current load value. If it is the first time through this loop after a screening loop, the current pointer is not changed. It then checks whether the confirmation loop has been executed more than five consecutive times and whether the top surface pointer has not been found. In general this latter test will be false if control passed to the screening loop because the current load was greater than the maximum expected non-event load. Otherwise, it would be true since the screening loop does not reset the top surface pointer when it calls the confirmation loop by reason of having the load signal greater than the maximum expected event load (that is, an error or fault condition). Thus, only when the confirmation has been called five times in a row for reasons other than faulty or excessive load signal value will the two-part test be satisfied. In that case the confirmation loop sets the top surface pointer to five less than the current array position, thereby identifying the position of the measurement foot at the first of the data sets which caused the confirmation loop to be called five times in a row. The top ZLC measurement thickness is taken as the thickness position corresponding to this data point.

At this point, the confirmation loop also checks whether the current load is less than the maximum expected non event load and also less than the maximum expected event load, and if so it passes the current array position to the screening loop and re-initializes the run variables. In general the screening loop and confirmation continue to run as long as data points have been accumulated, that is, as long as the current array position is less than the maximum number of data pairs (if working on stored data), or until it takes several complete measurement cycles (if analyzing in real time). After the confirmation loop has been entered five times in succession and passed the test, the current top surface pointer position which it sets (i.e., five less than the current array position at the fifth run through) is taken as the top ZLC position. The loop then initializes run variables and again screens data points to develop another measurement. Once a collection of measurements have been made, the software undertakes a data management protocol to perform regression analysis on the top ZLC measurement results from this run and the subsequent or previous ones. That is, it calculates and displays the current top ZLC measurement, the average top ZLC of all runs, and the specimen count. Thus the overall program operation screens the load position pairs to detect a pattern indicating contact of the workpiece, determines the initial position when some significant load change was detected indicative of the initial or top zero load contact position, and finally accumulates and smoothes the top ZLC reading from a plurality of runs to get a meaningful measurement.

In addition to the top ZLC measurement, the processor may in a straightforward manner interface with the measurement foot controller to continue to drive the measurement foot downward until a predetermined number of steps following top ZLC have been taken, or until a predetermined absolute load is detected, or until a set of coordinates relating load and position along a compression curve have been compiled. In the case of the measurement foot position being advanced until a predetermined load is met, the position reading will correspond in a direct way with a conventional TAPPI measurement. This may be useful where TAPPI measurements are necessary for some empirically derived product standards or process control. In addition, this ability to translate between true zero load caliper readings and TAPPI measurements allows one to correlate historical sets of information obtained with different materials using different test protocols at a different time, and opens new avenues for understanding the thickness properties of thin webs of material.

Figure 4:
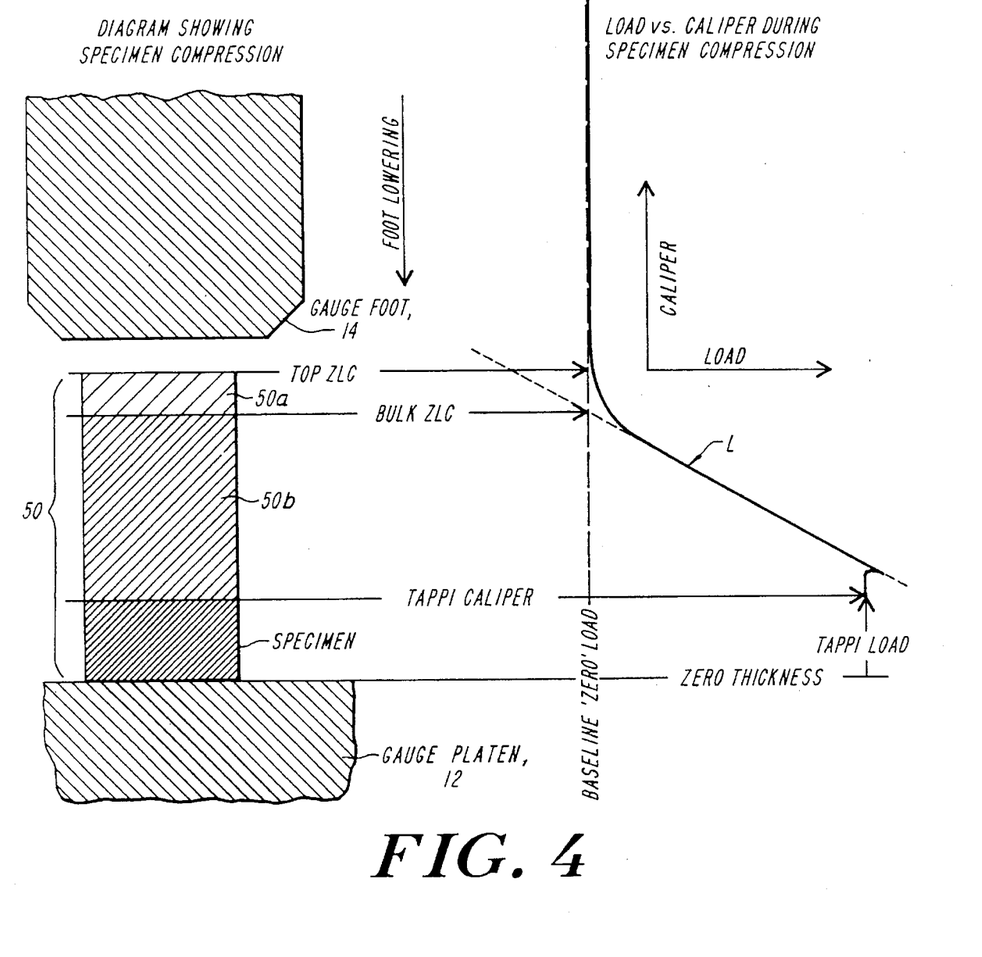
FIG. 4 illustrates measurement data with the apparatus for compressible homogenous material.

FIG. 4 illustrates advance of the measurement foot and the form of load/position curve for a typical compressible, homogenous medium. A specimen 50 is placed on the anvil 12 and contacted by the measurement foot 14 as it advances. Specimen 50 is illustrated as having an upper surface region 50a in which contact is first established, and an adjacent region 50b in which the measurement foot starts to experience a compressive resistance that is more or less a linear function L of position. This latter region exhibits the bulk compressive characteristic of the medium, and in general is attained fairly quickly, that is as the foot advances a thousandth of an inch or less beyond the top ZLC position, during which time the load climbs quickly from zero to about one-half psi.

As shown in the FIGURE, the tangent to the compression function L intersects the zero load value at the bulk ZLC thickness. The processor readily solves for this position coordinate. As the measurement foot advances, the load climbs to 7.3 psi. At this point, the processor preferably implements a different control algorithm for the measurement foot, checking the load as the specimen compresses and relaxes, advancing the foot only when the load dips below 7.3 psi. Thus it controls motion of the foot to provide a constant load of 7.3 psi. The data set corresponding to this control regimen appears at the right hand edge of the FIGURE, and is a vertical line at load=7.3 psi. The microprocessor counts time, and determines the foot position after holding the 7.3 psi load constant for three seconds; this provides a conventional TAPPI thickness measurement of the specimen.

Figure 5:
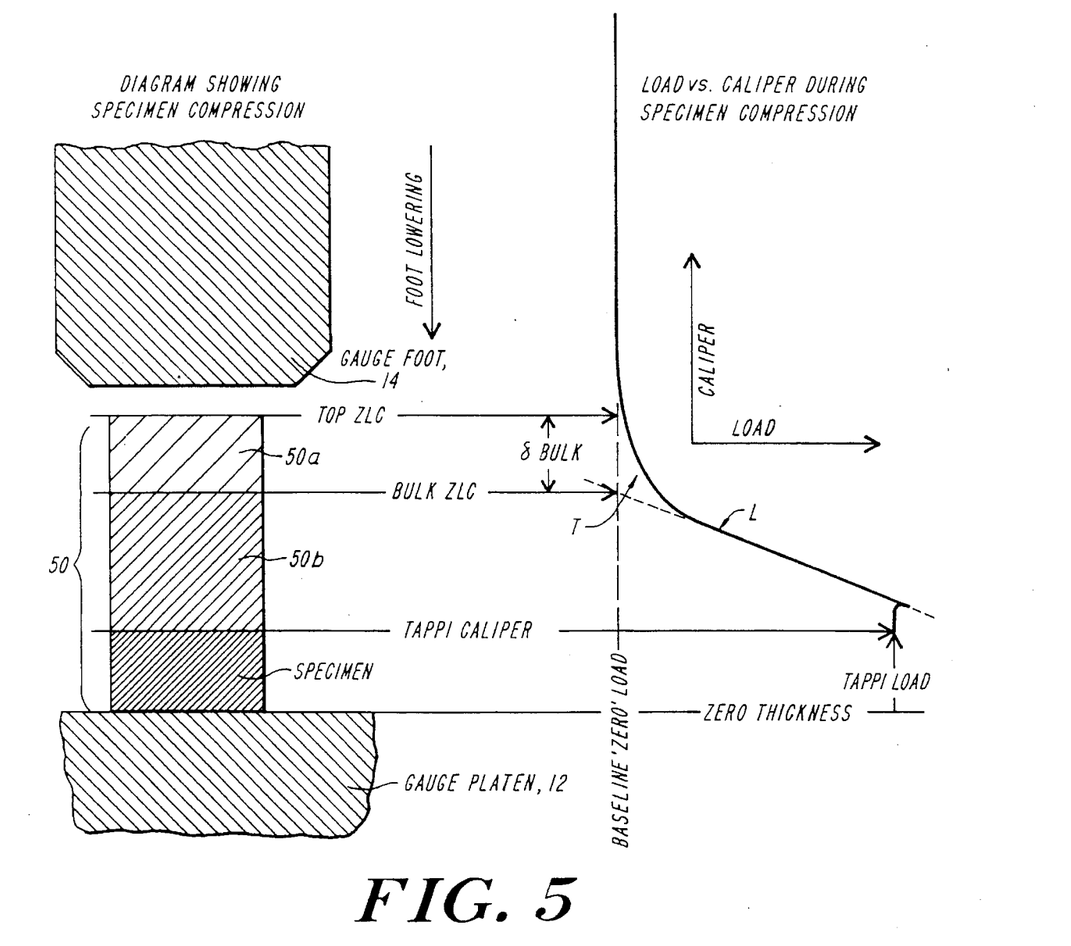
FIG. 5 illustrates measurement data of the apparatus for compressible, nonhomogenous material.
Figure 6:
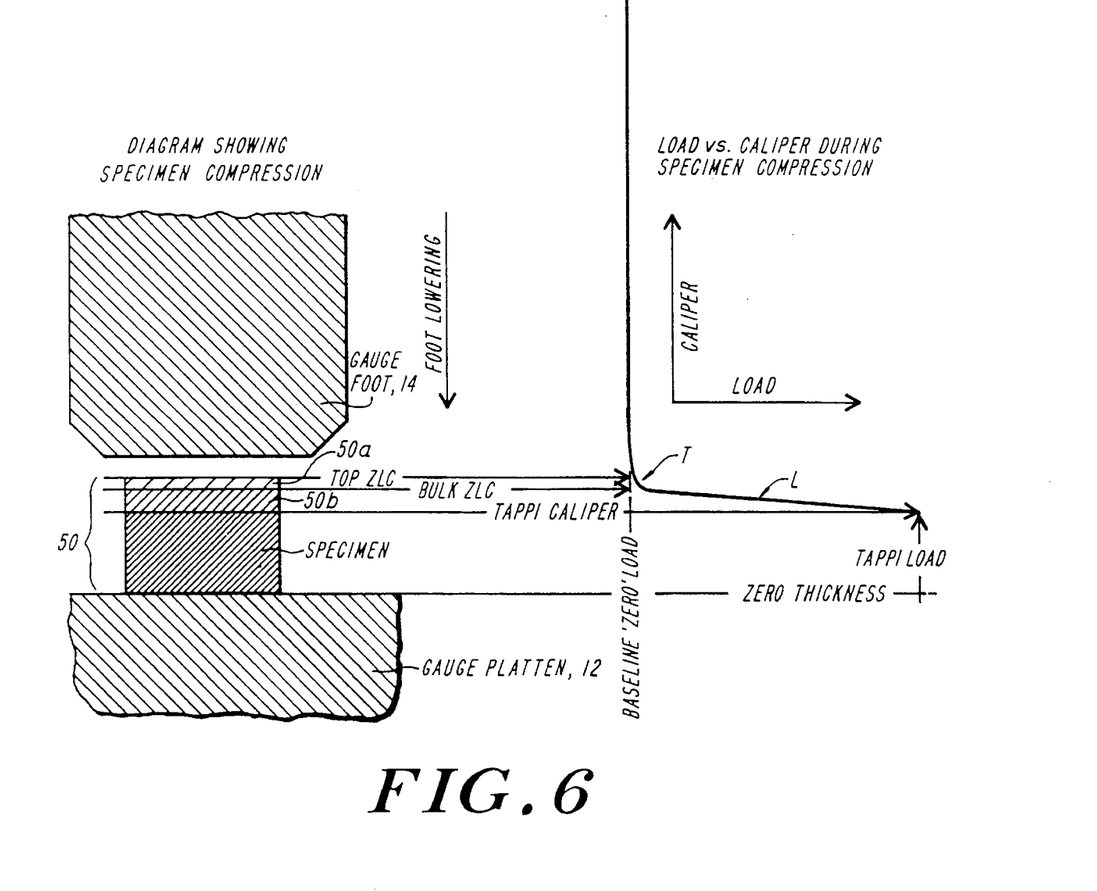
FIG. 6 illustrates measurement data of the apparatus for rigid material.

FIG. 5 shows a similar figure, illustrating operation on a compressible, non-homogenous specimen. In this case, the initial transition region between zero load and the onset of a linear compression curve is somewhat larger, resulting in a greater foot travel $\delta_{bulk}$ between top ZLC and the extrapolated bulk ZLC position. The bulk ZLC position, however, is still given by the intercept of the linear compression curve L with the zero load vertical line.

What is claimed is:

1. A measurement apparatus comprising a caliper having a first contact face for supporting an article to be measured, and a movable contact face for moving into contact with the article supported on said first face position means for developing a sequence of position signals indicative of position of said movable contact face as said movable contact face moves opposed to said first contact face, so that when it contacts the article, the position means indicates thickness of the article load means for developing a sequence of load signals indicative of load exerted on one of said contact faces, and processing means operative on said sequences of load signals and position signals for determining zero load thickness of the article wherein said processing means detects an initial load signal level and determines when the load signal differs from said initial load by an amount greater than a noise band.

2. A measurement apparatus according to claim 1, wherein said load means includes a load cell operatively connected to said first contact face, and said processing means adaptively determines a load signal level at successive positions of said movable contact face.

3. A measurement apparatus according to claim 1, wherein said first contact face forms a stationary anvil which includes a load cell.

4. A measurement apparatus according to claim 1, wherein the processing means adaptively sets the noise band.

5. A measurement apparatus according to claim 1, wherein the processing means identifies a compression curve of load and position signals to determine an initial contact position indicative of said zero load thickness.

6. A measurement apparatus according to claim 1, wherein said processing means includes means for graphically determining an empirical compressed state measurement from said load and position signals.

7. Apparatus according to claim 1, wherein the load and position signals are scaled, and said processing means processes integer-valued signals without floating point arithmetical operations.

8. Apparatus according to claim 7, wherein said processing means forms a stack for processing a window of $2^n$ load signals, such that as load cell signals are successively generated a set of $2^n$ most recent signals reside in the processing means.

9. Apparatus according to claim 1, wherein said processing means processes said load signals to compensate for output signal drift.

10. Apparatus according to claim 1, wherein said position means resolves position to within approximately 0.0001 inches (0.0025 mm).

11. Apparatus according to claim 1, wherein the processing means includes means for controlling the movable contact face to exert a fixed load for a defined period of time, and the processing means processes detected position signals to determine a TAPPI measurement.

12. Apparatus according to claim 1, wherein the processing means determines a relaxed compressed position measurement at a linear portion of a load/position curve.

13. Apparatus according to claim 1, wherein the processing means processes in different modes to determine any of several different thickness measurements having primary application to materials selected from among at least two of compressible homogenous, compressible inhomogenous, and substantially incompressible materials.

14. A measurement apparatus comprising a caliper having a first contact face for supporting an article to be measured, and a movable contact face for moving into contact with the article supported on said first face position means for developing a sequence of position signals indicative of position of said movable contact face as said movable contact face moves opposed to said first contact face, so that when it contacts the article, the position means indicates thickness of the article load means for developing a sequence of load signals indicative of load exerted on one of said contact faces, and processing means operative on said sequences of load signals and position signals for determining zero load thickness of the article wherein the processing means includes means for identifying a linear region of a load/position compression curve, and means for deriving an intercept of a tangent to said linear region.

15. Apparatus according to claim 14, wherein said intercept is a bulk zero load caliper measurement.

16. A method of making a zero load thickness measurement of an article, such method comprising the steps of placing the article between first and second faces and advancing at least one of the faces so that it contacts the article and the article is held between the first and second faces, monitoring position of the advancing face while sensing load against the other face, storing position and processing the position and load to determine a normal pattern, and detecting a change in said normal pattern to identify a stored position as the thickness measurement.

17. A method according to claim 16, wherein the processing means determines said thickness position in relation to a linear portion of a compression curve.

18. A method according to claim 16, wherein the processing means detects said thickness as an initial position in relation to a curved portion of a compression curve.

19. A measurement apparatus comprising a caliper having a first contact face for supporting an article to be measured, and a movable contact face for moving into contact with the article supported on said first face position means for developing a position signal indicative of position of said movable contact face as said movable contact face moves opposed to said first contact face load means for developing a of load signal indicative of load exerted on one of said contact faces, and processing means operative on said load signal and position signal for determining zero load thickness of the article, wherein the processing means
ii) stores said position signal, and
iii) processes said load signal to identify a pattern of load change, identifying from said pattern a stored position signal corresponding to a zero load contact position of said movable contact face with the article.

* * * * *